(12) United States Patent
Holton et al.

(10) Patent No.: US 9,879,308 B2
(45) Date of Patent: Jan. 30, 2018

(54) APPARATUS FOR EX VIVO MICROFLUIDIC ANALYSIS OF BIOLOGIC SAMPLES

(71) Applicant: The Charles Stark Draper Laboratory, Inc., Cambridge, MA (US)

(72) Inventors: Angela Holton, Tampa, FL (US); Alla Gimbel, Tampa, FL (US); David Landis, Cambridge, MA (US); Abigail Spencer, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 493 days.

(21) Appl. No.: 14/586,577

(22) Filed: Dec. 30, 2014

(65) Prior Publication Data

US 2015/0118742 A1   Apr. 30, 2015

Related U.S. Application Data

(62) Division of application No. 14/070,444, filed on Nov. 1, 2013, now abandoned.

(Continued)

(51) Int. Cl.
*G01N 33/50* (2006.01)
*C12Q 1/68* (2006.01)
(Continued)

(52) U.S. Cl.
CPC .......... *C12Q 1/68* (2013.01); *B01L 3/502761* (2013.01); *C12M 23/16* (2013.01);
(Continued)

(58) Field of Classification Search
CPC ..... B01L 2200/0668; B01L 2400/0487; B01L 2400/086; B01L 3/502761; C12M 23/16;
(Continued)

(56) References Cited

U.S. PATENT DOCUMENTS

| 2006/0000772 A1* | 1/2006 | Sano ................... B01D 67/0062 |
| | | 210/635 |
| 2009/0136982 A1* | 5/2009 | Tang ....................... B01F 5/102 |
| | | 435/29 |

(Continued)

FOREIGN PATENT DOCUMENTS

| EP | 0 803 288 A2 | 10/1997 |
| WO | 2012050981 A1 | 4/2012 |

OTHER PUBLICATIONS

Doran, Marianne, Fine-Needle Aspiration Biopsy for Ocular and Orbital Tumors, Oncology, EyeNet, pp. 37-39, Jul. 2012.

(Continued)

*Primary Examiner* — Jennifer Wecker
(74) *Attorney, Agent, or Firm* — McDermott Will & Emery LLP

(57) ABSTRACT

Systems and methods for culturing and monitoring, ex vivo, pharmacologic and metabolic response in a biological sample, including receiving at a fluidic apparatus the biological sample retrieved from the patient, retaining the biological sample within a channel of the fluidic apparatus, providing for the culture of the biological sample within the channel of the fluidic apparatus, flowing a fluid past the biological sample, retrieving and analyzing the fluid to determine a pharmacologic and/or metabolic response of the sample.

11 Claims, 18 Drawing Sheets

Related U.S. Application Data

(60) Provisional application No. 61/721,183, filed on Nov. 1, 2012.

(51) Int. Cl.
  *C12M 3/06* (2006.01)
  *B01L 3/00* (2006.01)

(52) U.S. Cl.
  CPC ..... *G01N 33/5008* (2013.01); *G01N 33/5082* (2013.01); *B01L 2200/0668* (2013.01); *B01L 2400/0487* (2013.01); *B01L 2400/086* (2013.01); *G01N 2510/00* (2013.01)

(58) Field of Classification Search
  CPC .. C12Q 1/68; G01N 2510/00; G01N 33/5008; G01N 33/5082
  See application file for complete search history.

(56) References Cited

U.S. PATENT DOCUMENTS

| | | | |
|---|---|---|---|
| 2010/0216241 A1* | 8/2010 | Yu | C12M 25/06 435/395 |
| 2011/0136162 A1 | 6/2011 | Sun et al. | |
| 2011/0256574 A1* | 10/2011 | Zhang | B01L 3/502761 435/29 |
| 2012/0329082 A1* | 12/2012 | Viola | B01L 3/5027 435/13 |
| 2013/0005585 A1* | 1/2013 | Anderson | C12N 15/10 506/2 |
| 2014/0038279 A1* | 2/2014 | Ingber | C12M 25/02 435/297.2 |
| 2016/0018365 A1* | 1/2016 | Agah | B01J 20/223 73/23.41 |
| 2016/0279637 A1* | 9/2016 | Sarioglu | B01L 3/502746 |

OTHER PUBLICATIONS

FBNA. Procedure/diagnostic tests: interventional radiology. Clinical Center national Institutes of Health, pp. 1-5, 2010.

Hattersley et al., A Microfluidic System for Testing the Responses of Head and Neck Squamous Cell Carcinoma Tissue Biopsies to Treatment with Chemotherapy Drugs, Annals of biomedical engineering, vol. 40, No. 6, pp. 1277-1288 (Jun. 2012).

International Search Report and Written Opinion dated Jan. 31, 2014 in PCT Application No. PCT/US2013/068168 (9 pages).

Kim, et al. In-Situ Synthesized and Patterned Nanowire Arrays in Microfluidic Channel for Particle Trapping and Cell Lysis Applications, 15th International Conference on Miniaturized Systems for Chemistry and Life Sciences, pp. 1789-1791, Oct. 2011.

Prot et al, The Current Status of Alternative to Animal Testing and Predictive Toxicology Methods Using Liver Microfluidic Biochips, Annals of biomedical engineering, vol. 40, No. 6, pp. 1228-1243 (Jun. 2012).

Sorger, Peter K., Microfluidics closes in on point-of-care assays, Nature Biotechnology, vol. 26, No. 12, pp. 1345-1346 (Dec. 2008).

U.S. Office Action in U.S. Appl. No. 14/070,444 dated Mar. 4, 2015.

Vickerman et al., Design, fabrication and implementation of a novel multi-parameter control microfluidic platform for three-dimensional cell culture and real-time imaging, Lab on a Chip, vol. 8, No. 9, pp. 1468-1477 (Jul. 2008).

Zhang et al, Microfluidics and cancer: are we there yet?, Biomed Microdevices, vol. 15, No. 4, pp. 595-609 (Jan. 2013).

* cited by examiner

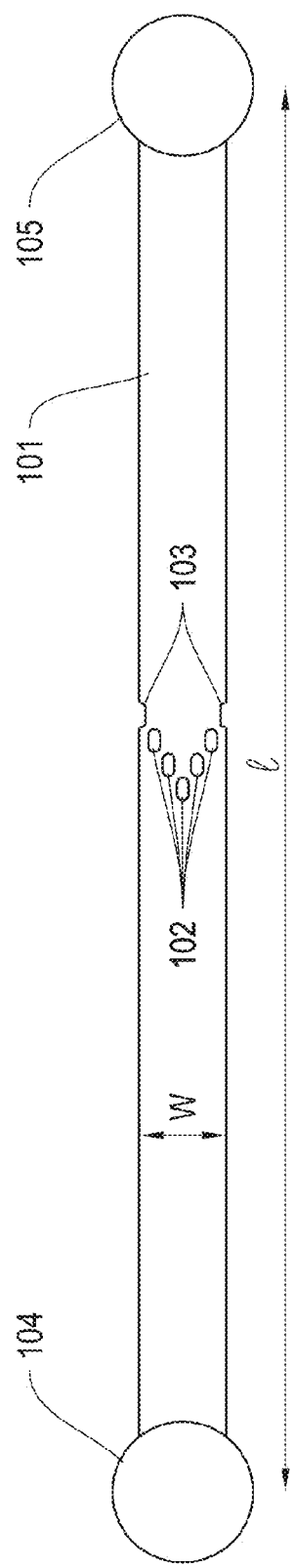
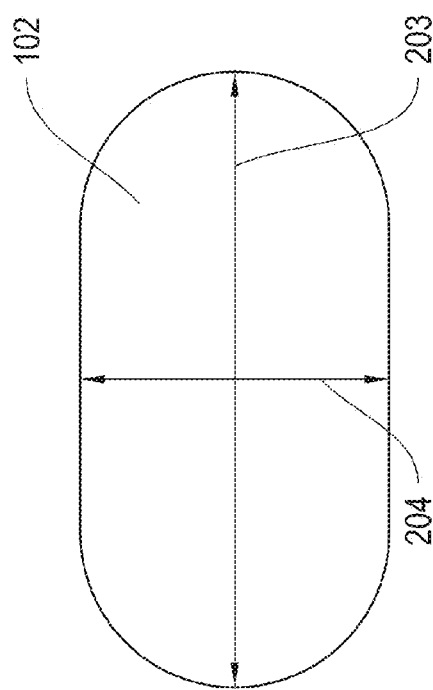
FIG. 1B
FIG. 1C

DEVICE ANALYSIS
CONTROL
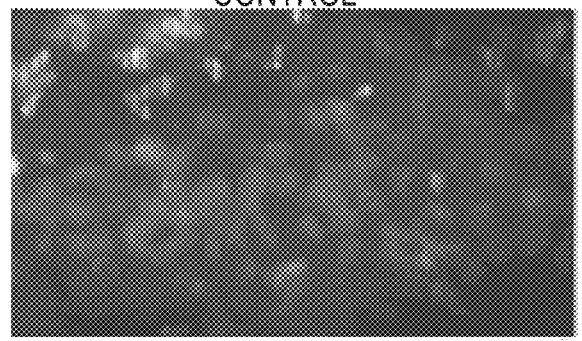
GEMCITABINE/MK
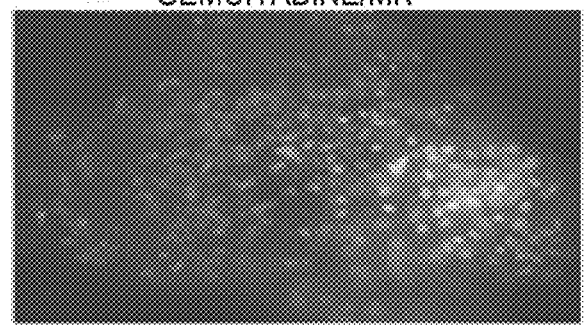
GEMCITABINE ALONE
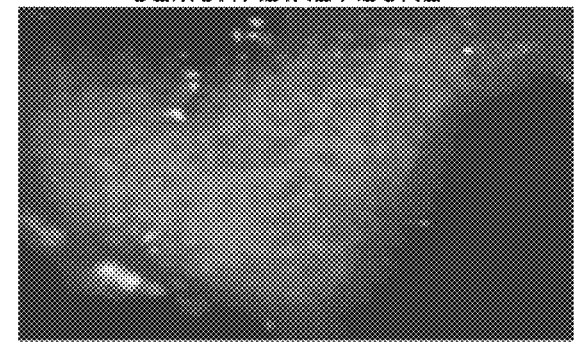
MK ALONE
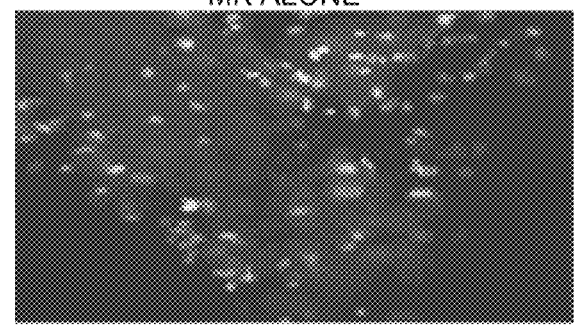
FIG. 7C

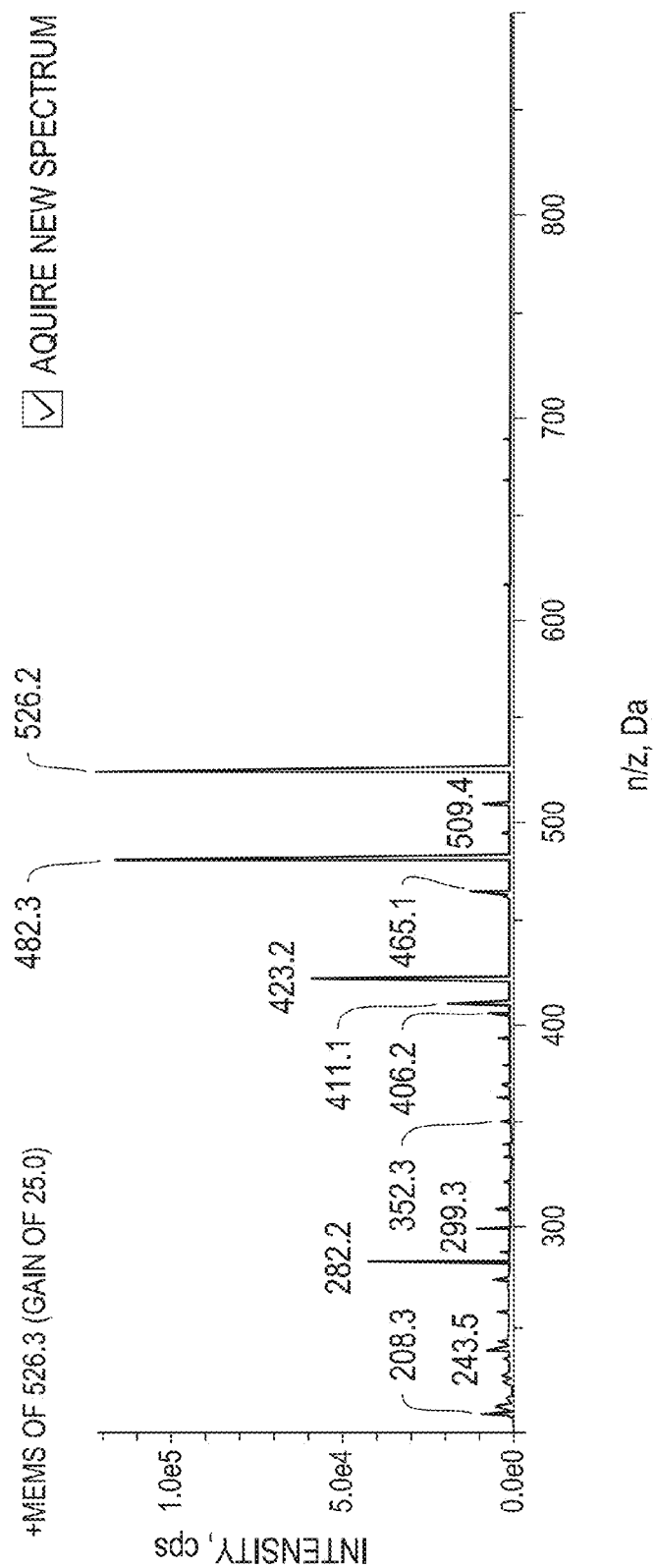
FIG. 8 (continuation 1)

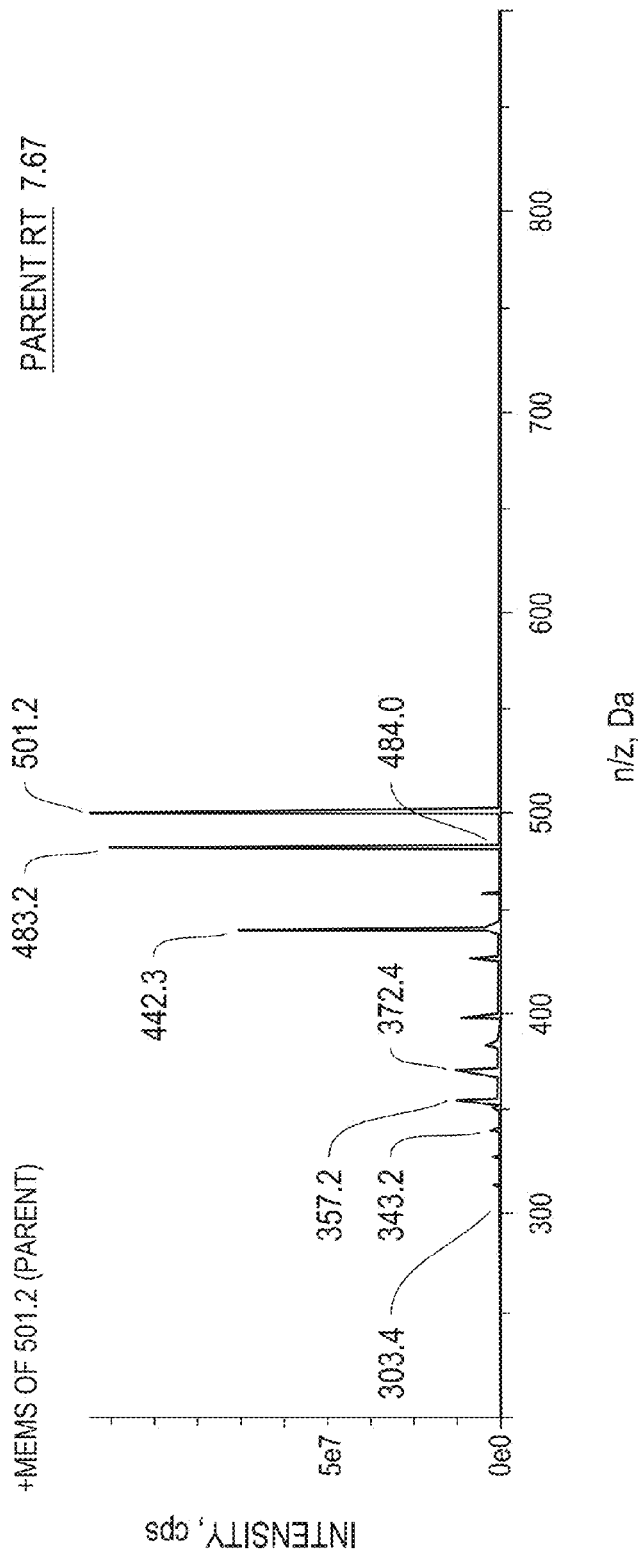
FIG. 8 (continuation 2)

APPARATUS FOR EX VIVO MICROFLUIDIC ANALYSIS OF BIOLOGIC SAMPLES

CROSS-REFERENCE TO RELATED PATENT APPLICATIONS

The present application is a divisional of U.S. application Ser. No. 14/070,444, entitled "Ex Vivo Microfluidic Analysis Of Biologic Samples," filed on Nov. 1, 2013, and which claims priority to and benefit of U.S. Provisional Application No. 61/721,183, filed Nov. 1, 2012, the entire contents of which are incorporated by reference herein in their entirety.

TECHNICAL FIELD

This invention relates to culturing and monitoring a biological sample.

BACKGROUND

Within the pharmaceutical and biotech industries, there is significant interest in identifying screening systems that are more clinically relevant in predicting physiological responses in normal and diseased human tissues to reduce the incidence of costly late-stage failures during pharmaceutical clinical trials, as well as to reduce the use of animals in drug testing. Empiric approaches in cancer treatment result in many patients receiving multiple cycles of therapy without success before the lack of efficacy is identified.

Identification of therapies and individualized therapeutics is of critical importance to cancer clinical research. The development of clinically relevant assays to predict drug efficacy would allow the identification of patients who may benefit from a certain therapy while sparing others from the side effects of futile treatment.

The ability to improve patient selection and a means of enriching clinical trials to better identify effective candidate regimens for patients with given tumor types is the future of molecular medicine. Nevertheless, ex vivo chemosensitivity assays have never really borne fruit despite waves of optimism in the past mainly due to failure to recapitulate the in vivo conditions in an ex vivo environment.

SUMMARY

According to one aspect of the disclosure, a fluidic apparatus includes a substrate, a channel located within the substrate, and a concave retaining barrier located within the channel. The channel is configured to receive a biological sample and to carry a fluid flow across the biological sample. The concave retaining barrier is configured to retain the biological sample. The geometry of the concave retaining barrier is configured to allow the fluid flowing through the channel to induce interstitial flow of the fluid through the biological sample as to perfuse the biological sample with the fluid while maintaining shear rates at the biological sample within a range of between about 0.375 and 0.500 dynes/cm$^2$.

In some implementations, the concave retaining barrier includes a plurality of posts extending from the floor of the channel to the top of the channel. In some implementations, the plurality of posts includes between three to ten free-standing posts, which extend the full height of the channel and at least one embedded post extending out from a channel sidewall. In some implementations, the concave retaining barrier includes five free-standing posts and two embedded posts.

In some implementations, the adjacent posts are spaced apart from one another to have a lateral separation across of the between about 20 µm-about 30 µm. In some implementations, the shortest distance between any two adjacent posts is between about 65 µm-85 µm. In some implementations, the outer most free-standing post of the plurality of posts is spaced between about 65 µm-85 µm away from a nearest channel sidewall.

In some implementations, the fluidic apparatus also includes a fluid supply configured to flow a fluid through the channel. In some implementations, the fluid supply includes a closed loop fluid supply configured to reroute fluid already flowed through a distal end of the channel back through a proximal end of the channel.

In some implementations, the fluidic apparatus also includes a fluid extractor configured to extract a sample of the fluid after it has flowed through to channel.

In some implementations, the fluidic apparatus also includes an optical sensor for optically monitoring a state of a biological sample located within the retaining barrier.

In some implementations, the biological sample is between about 100 and about 500 microns in diameter.

According to another aspect of the disclosure, a method of assessing the impact of a pharmacological agent on an ex vivo tissue sample includes introducing a tissue sample having a diameter of between about 100-500 microns into a concave retaining barrier formed in a flow channel, introducing a fluid including the pharmacological agent to the channel such that the fluid flows through the channel across the tissue sample, collecting a portion of the fluid, and analyzing the collected fluid portion for evidence of pharmacological impact on the tissue sample. The channel and concave retaining barrier are configured to induce interstitial flow of the fluid through the tissue sample, such that the fluid perfuses through the tissue sample. In some implementations, the evidence of pharmacological impact includes evidence of cell death.

In some implementations, the method also includes capturing an image of the tissue sample after flowing the fluid through the channel and analyzing the captured image for evidence of pharmacological impact on the tissue sample.

In some implementations, the fluid flows through the channel at a rate of about 500 microliters per hour. In some implementations, the tissue sample includes a tissue sample collected using fine-needle biopsy (FNBA).

In some implementations, the concave retaining barrier includes a plurality of posts extending from the floor of the channel to the top of the channel. In some implementations, the plurality of posts includes between three to ten free-standing posts extending the full height of the channel and at least one embedded post extending out from a channel sidewall.

In other implementations, the method includes introducing a second tissue sample having a diameter of between about 100-500 microns into a second concave retaining barrier formed in a second flow channel, introducing a second fluid including a second pharmacological agent to the channel such that the fluid flows through the channel across the second tissue sample, collecting a portion of the second fluid, and analyzing the collected fluid portion for evidence of pharmacological impact on the second tissue sample, and comparing the pharmacological impacts of the first and second pharmacological agents. In some implementations, the selection of the first or second pharmacological agents for treatment of an animal is based on the comparison of the pharmacological impacts. In some implementations, the animal is a source of the first and second tissue samples.

The details of one or more implementations of the invention are set forth in the accompanying drawings and the description below. Other features, objects, and advantages of the invention will be apparent from the description and drawings, and from the claims.

DESCRIPTION OF DRAWINGS

The apparatus is explained in even greater detail in the following example drawings. The drawings are merely examples to illustrate the structure of the apparatus and certain features that may be used singularly or in combination with other features. The present technology is not be limited to the implementations shown.

FIG. 1B is a diagram showing an exemplification of a channel.

FIG. 1C is a diagram showing an exemplification of dimensions of a free standing post.

FIG. 7C provides images of tumor response in a microfluidic apparatus ex vivo.

DETAILED DESCRIPTION

To provide an overall understanding of the invention, certain illustrative implementations will now be described, including apparatuses and methods for culturing cells in a biomimetic environment. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Provided are apparatuses, systems, and methods for culturing and monitoring, ex vivo, pharmacologic, and metabolic response in a biological sample. For example, the present disclosure includes a cost effective method that monitors patient driven pharmacologic and metabolic responses in an ex vivo micro-scale fluidic apparatus utilizing fine-needle aspiration biopsy (FNAB) samples or other tissue samples through which a test agent can perfuse. Additionally, or alternatively, the present technology is directed to a standardized tumor microenvironment model to individualize cancer therapy selection using a microfluidics assay susbtrate that utilizes microscopic tumor tissue obtained by fine needle aspiration biopsy (FNAB) or other extraction method to analyze tumor response to conventional and targeted anti-cancer drugs.

Biomolecular sensors for high throughput real-time monitoring of drug response are optionally integrated with this platform. While the disclosure focuses on a single channel apparatus for ease of explanation, other apparatuses having multiple channels for high throughput multi-drug analysis at various drug concentrations can also be used. The apparatuses can also be used for multi-tissue interactions within a complex system of pharmacodynamic/pharmacokinetic/proteomic/metabolomic and for genomic processes that are influenced by multiple organ systems in vivo to generate a reproducible, repeatable clinical model for patient specific responses to trials of chemotherapies.

Figure 1A:
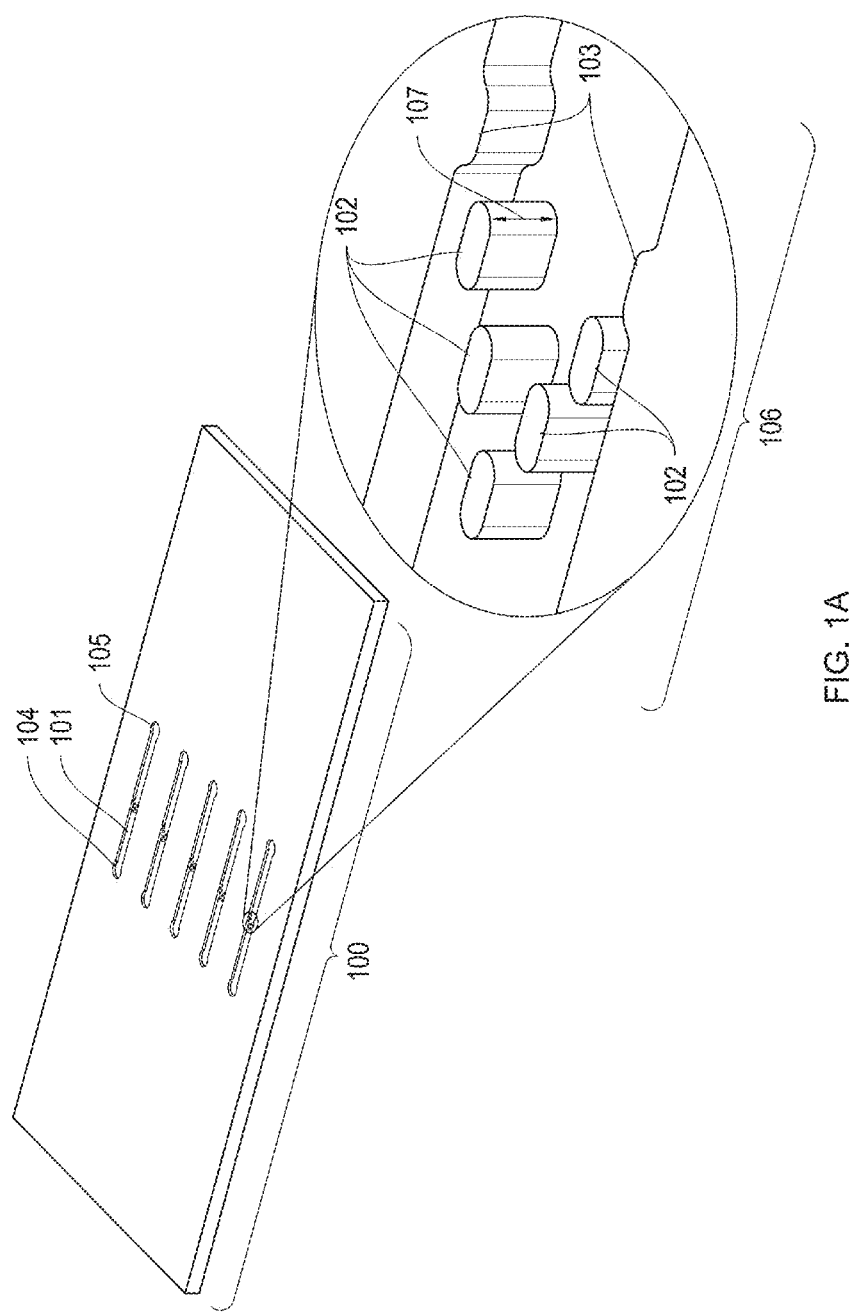
FIG. 1A is a diagram showing an exemplification of a micro-scale microfluidic apparatus and its retaining element.

The fluidic apparatus may include a substrate, a channel located within the substrate, a retaining element located within the channel for retaining the biological sample, a supply apparatus for supplying a fluid to the channel, a retrieval apparatus for retrieving fluid from the channel, and a visual field for providing visual observation of the channel. A non-limiting example of a three-dimensional (3-D) microscale fluidics apparatus is provided in FIGS. 1A-D. FIG. 1A is a diagram of a micro-scale fluidics apparatus 100 with five channels 101. In some implementations, the micro-scale fluidics substrate has one channel, or two channels, or three channels, or four channel, or five channels, or six channels. In some implementations, the micro-scale fluidics substrate has up to or more than ten channels. In some implementations, a high-throughput micro-scale fluidics may be produced containing a hundred or more channels. The biological sample inserted into each channel can be the same for each channel, different for each channel, or a combination thereof.

FIG. 1B is a diagram of a single channel 101. The channel 101 is about 10 mm in length (1) and about 615 μm in width (w). In various implementations, the channel 101 is between about 5 mm to about 20 mm long, between about 400 μm to about 1000 μm wide, and between about 75 μm to about 500 μm high. The channel 101 has a fluid inlet 105, a fluid outlet 104, and a concave retaining barrier 106.

The concave retaining barrier 106 in the channel 101 includes five free standing posts 102 and a pair of embedded posts 103 in the sidewalls of the channel 101. The free standing posts 102 and embedded posts 103 are arranged in a V-configuration that points in the direction of the flow of fluid through the channel 101. The concave retaining barrier 106 is used to hold a biological sample in place. In some implementations, the concave retaining barrier 106 includes more than five free standing posts. In some other implementations, there are six, seven, eight, nine, or ten free standing posts per concave retaining barrier 106. In some other implementations, there are less than five free standing posts.

In some implementations, instead of being arranged in a V-configuration, the free standing posts 102 of the concave retaining barrier 106 are configured in a semi-circle formation, U-shape configuration, or any other shape concave with respect to the direction of flow through the channel 101.

In some implementations, there is more than one concave retaining barrier 106 per channel 101. For example, in some implementations, there are two, three, four, or five concave retaining barriers 106 in a single channel 101. In some implementations, the multiple concave retaining barriers are lined up along the length of the channel creating a series of concave retaining barriers. In other implementations, the multiple concave retaining barriers are lined up across the width of the channel forming a line of concave retaining barriers. In some implementations, each of the concave retaining barriers 106 in a channel 101 are identical. In other implementations, the retaining elements are formed from posts having different dimensions and spacing to trap tissue samples of different sizes. For example, the posts and paths between the posts may shrink progressively down the length of the channel to capture progressively smaller tissue samples.

As shown in FIGS. 1A and 1C, the free standing posts 102 are about 150 μm long 203, about 75 μm wide 204, and about 125 μm high 107. In some implementations, the free standing posts are between about 50 μm to about 200 μm long, between about 50 μm to about 100 μm wide, and between about 50 μm to about 500 μm high. The embedded posts 103 are about 150 μm long and about 125 μm high. In some implementations, the embedded posts are between about 25 μm to about 175 μm long and between about 100 μm to about 150 μm high. In some implementations, the free standing posts 102 have between about a 2:1 to about a 3:1 length to width ratio. In some implementations, the free standing posts 102 and/or the embedded posts 103 are as high as the channel 101. In other implementations, the height of the channel has up to about a 1:2 ratio compared to the diameter of the biological sample.

Figure 1D:
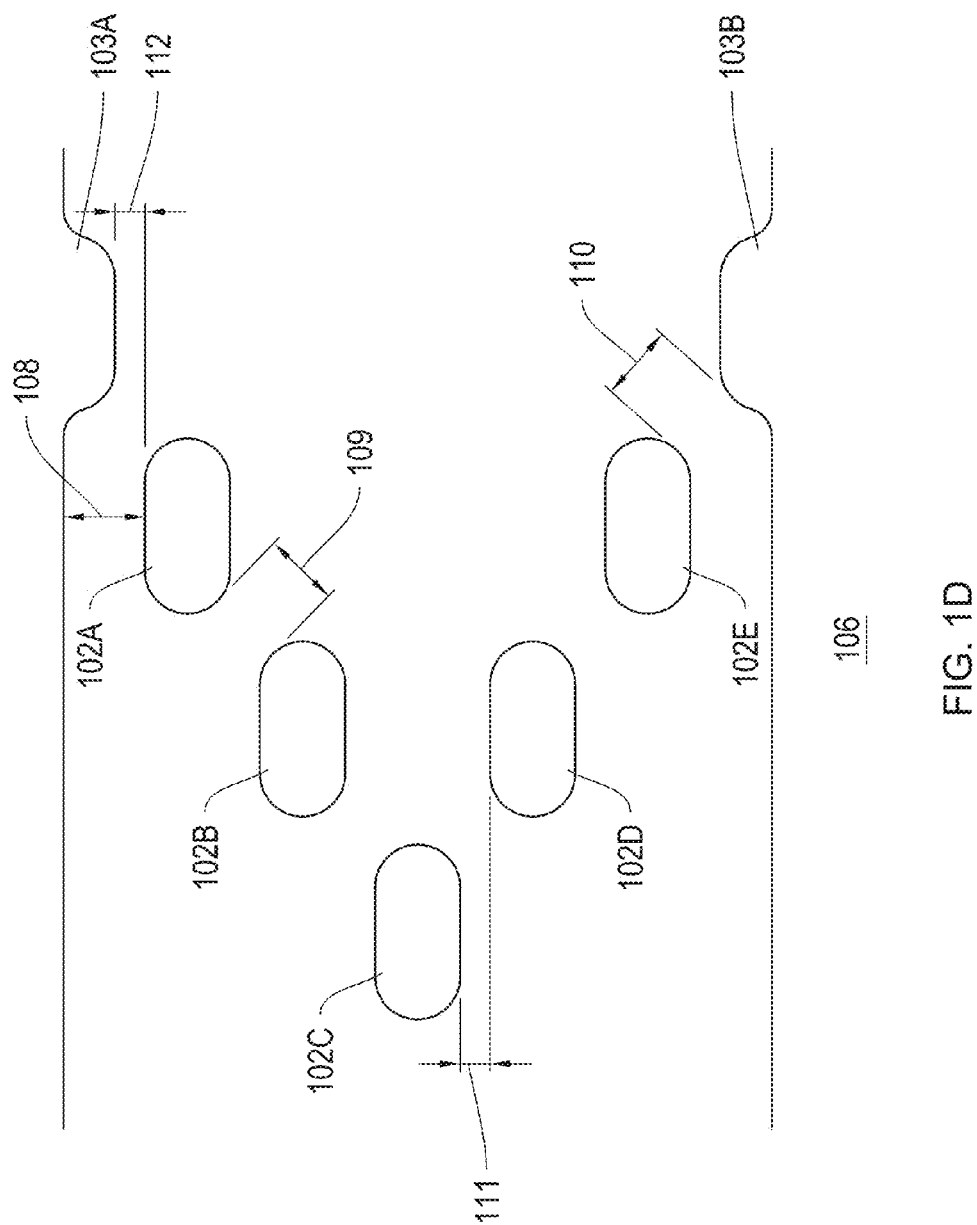
FIG. 1D is a diagram showing an exemplification of a retaining element.

FIG. 1D is a diagram showing exemplary spacing of the embedded posts 103A and 103B and free standing posts 102A-102E of the concave retaining barrier 106. In some implementations, the free standing posts 102 and embedded posts 103 are aligned such that the leading ends of complimentary posts are aligned, e.g., the leading ends of 102A and 102E are aligned. Additionally, or alternatively, in some implementations, the leading edge of one free standing post is aligned with the trailing edge of the next free standing post in the channel 101, e.g., the leading edge of 102B may be aligned with the trailing edge of 102C.

The distance 205 between the sidewalls of the freestanding posts 102A and 102E closest to the channel sidewall is about 70 μm. In some implementations, the distance 108 between the sidewalls of the freestanding posts 102A and 102E closest to the channel sidewall is between about 60 μm to about 80 μm. The diagonal distance 110 between the closest points of the freestanding posts 102A and 102E closest to the embedded posts 103A and 103B is about 75 μm. In some other implementations, the diagonal distance 110 between the closest points of the freestanding posts 102A and 102E closest to the embedded posts 103A and 103B is between about 65 μm to about 85 μm. The lateral spacing 112 between the outer walls of free standing posts 102A and 102E and the outer walls of embedded posts 103A and 103B is about 25 μm. In some implementations, the lateral distance 112 between outer walls of free standing posts and the outer walls of embedded posts is between about 20 μm to 40 μm.

The lateral spacing 111 between the walls of adjacent free standing posts, e.g., 102A to 102B, 102B to 102C, 102C to 102D, and 102D to 102E, is about 25 μm. In some implementations, the lateral distance 111 between the outer walls of adjacent free standing posts is between about 20 μm to 40 μm. The diagonal distance 109 between the closest points of two adjacent free standing posts, e.g., 102A to 102B, 102B to 102C, 102C to 102D, and 102D to 102E, is about 75 μm. In some other implementations, the diagonal distance 109 between the closest points of two adjacent free standing posts is between about 65 μm to 85 μm.

The geometry of the channel 101 and the spacing of the components of the concave retaining barrier 106 are selected for their beneficial characteristics with relation to culturing tissue samples having sizes on the order of 300 μm in diameter and smaller. The post sizing and spacing provides for fluid dynamics, including flow rate, shear rate, and pressure, that approximate in vivo conditions. As a result culturing the biological sample in the channel environment allows for the biological sample to remain intact without the triggering of shear related cellular responses. In some implementations, the flow rate is about 100 μl/hr, or about 250 μl/hr, or about 500 μl/hr, or about 1000 μl/hr, or ranges between any two of these values. In some implementations, the geometry and flow rate are selected to achieve shear stress on the sample of about 0.350, or about 0.375, or about 0.400, or about 0.425, or about 0.450, or about 0.500 dyne/cm$^2$ or any value between any two of these values, which are physiologically relevant and which do not pose a significant disturbance to the system or sample. For example, in some implementations, the geometry and flow rates are selected to provide a shear rate of between about 0.375 and 0.500 dyne/cm$^2$. In some implementations, the flow rate and geometry are selected to provide a shear rate of about 0.389 dyne/cm$^2$.

The flow and shear rates within the channel 101 are affected by the width of the channel 202 and the spacing of the free standing posts 102 and embedded posts 103. A wide channel reduces interstitial flow to the biological sample, as the fluid is able to move around the sample, thus reducing contact and perfusion. A narrow channel can increase shear stress, which can lead to shear-induced activation of gene expression. Shear-induced activation of gene expression can lead to a biochemical adhesion cascade in the biological sample and tissue transformation. Additionally, some studies have shown that in changing the shear stress a tissue experiences over time the extracellular matrix proteins become altered changing the tumors potential for cell invasion, angiogenesis and tissue remodeling. Mechanotransduction induced changes in the biological sample can have adverse effects on the assaying of the biological sample. Each of these conditions is preferably avoided to effectively replicate the tissue response in vivo to the agent being tested as a snapshot in time of the patient's cancer.

The embedded posts 103 also help maintain improved flow parameters. A channel 101 without embedded posts 103, i.e., in which the channel walls are smooth and spaced apart from the nearest free standing post 102, decreases interstitial flow throughout the biological sample and drug perfusion as the space between the two outer most free standing posts 102 and the channel side wall provides a substantial path, which allows the fluid to flow around the biological sample. In addition, using conventional micromachining and injection molding processes, which would be applied for high volume manufacture, maintaining a narrow enough gap to obtain a desirable flow between the outer most free standing posts 102 and a smooth channel wall is impractical, if not impossible. The use of the embedded posts 103 substantially mitigates this issue.

Biological samples to be assayed are inserted into the concave retaining barrier 106. In some implementations, the biological samples are tumor or tissue samples. The biological samples are micron-scale samples. In some implementations the biological samples are between about 100 μm and about 500 μm in diameter, and in some implementations less than about 300 µm. For example, in some implementations, the biological samples are fine needle aspirate biopsy samples (FNABs).

The fluidic apparatus can be produced methods known in the art. By way of example, but not by limitation, methods for producing the fluidic apparatus include injection molding, micro-machining, heat and/or pressure embossing, and photolithography. In some implementations, the fluidic apparatus is substantially smooth along all surfaces, e.g., the bottom and sides of the flow channel, the free standing posts, and the embedded posts. This helps prevent vortices and eddy currents in the flow, as well as prevents undesirable cellular interaction with the surfaces of the channel and concave retaining barrier.

The fluidic apparatus can be fabricated from known materials in the art. In some implementations, the fluidic apparatus is transparent, allowing for real-time visual analysis of the biological sample. The materials selected for the fluidic apparatus is substantially transparent (i.e., greater than 50%) to light in the visible portion of the spectrum and down to wavelengths of about 200 nm or smaller.

In some implementations, the fluidic apparatus is made of optical glass or glass-like material. Exemplary optical glass materials include, but are not limited to, N-FK51A, N-PK52A, N-PK51, N-FK5, P-BK7, P-SK58A, P-SK57, P-SK57Q1, P-SK60, N-KZFS2, P-LAK35, P-LAF37, N-KZFS4, N-LAF33, N-KZFS11, P-LASF51, P-LASF47, P-LASF50, N-KZFS5, N-KZFS8, N-LASF46B, P-SF8, P-SF69, P-SF67, and P-SF68 (available from Schott, Inc). In some implementations, the fluidic apparatus includes a cover forming a top to the channel 101. In some implementations, the cover is made from the same material as the fluidic apparatus.

In some implementations, the fluidic apparatus is made from polymers. Exemplary polymers include, but are not limited to, polymethyl methacrylate (PMMA), polyamide (PA), polycarbonate, polystyrene, polydimethylsiloxane (PDMS), and cyclic olefin copolymer (COC).

Figure 1E:
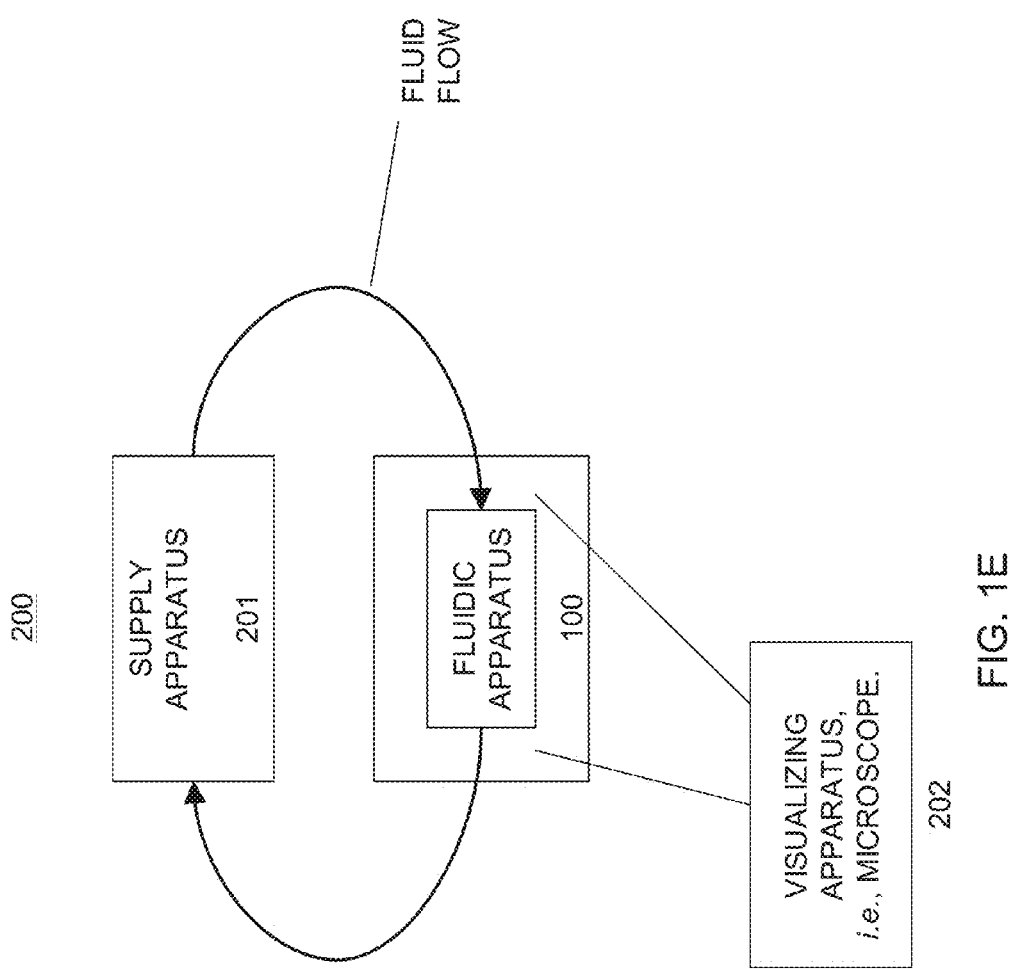
FIG. 1E is a diagram of a close-looped microfluidic system.
Figure 1F:
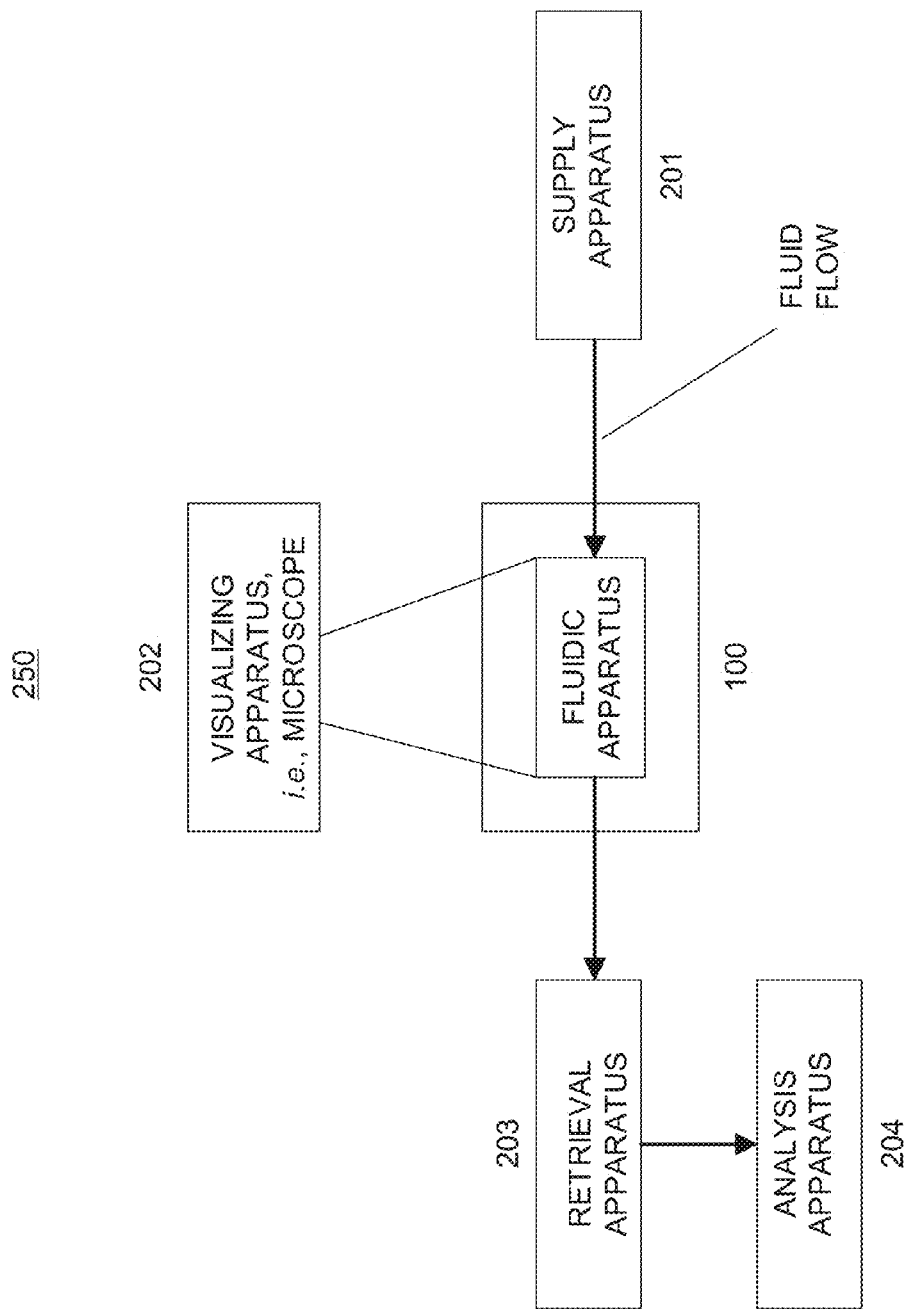
FIG. 1F is a diagram of a microfluidic system.

FIGS. 1E and 1F are diagrams showing exemplary microfluidic systems of the present disclosure for the analysis of ex vivo treatment of biological samples with drugs or therapeutic agents. FIG. 1E is an exemplary continuous closed-loop system 200. A supply apparatus 201 pumps fluid to the channel (or channels) of the fluidic apparatus 100 through a single fluid inlet (or multiple fluid inlets) and re-cycles the fluid received from the fluid outlet (or multiple fluid outlets), such that the biological sample is continuously perfused with the fluid. For example, the sample may be continuously perfused in a closed loop over a period of 7 days to determine the lifetime of FNAB samples in 3-D microenvironment platform. In some implementations, the sample is continuously perfused in a closed loop over a period of 12-24 hours, or 12-36 hours, or 12-48 hours, or 24-72 hours.

FIG. 1F is another exemplary continuous closed-loop system 250. A supply apparatus 201 pumps fluid to the channel (or channels) of the fluidic apparatus 100 through a single fluid inlet (or multiple fluid inlets) such that the biological sample is continuously perfused with the fluid. A retrieval apparatus 203 collects the fluid that has passed over/through the biological sample. In some implementations, the retrieval apparatus 203 provides the fluid to an analysis apparatus 204 to determine any pharmacologic and a metabolic responses associated with the sample and/or the fluid. In some implementations, the retrieval apparatus only collects a sample of the fluid and returns the remainder to the supply apparatus to provide a closed-loop fluidic system.

The microfluidic systems of FIG. 1E or 1F can also include a visualization apparatus 202, which can be configured to provide for visual observation using, for example, an inverted tissue culture microscope. For example, a Zeiss Axio Observer with ApoTome technology may be used for gross morphological measurements to determine cell growth and death in the microfluidics channels and resulting architecture and presence of differentiation. In addition, the visualization apparatus 202 may also include image sensors for capturing optical information from the sample for wavelengths of light ranging from the visible spectrum down to about 200 nm.

Figure 2A:
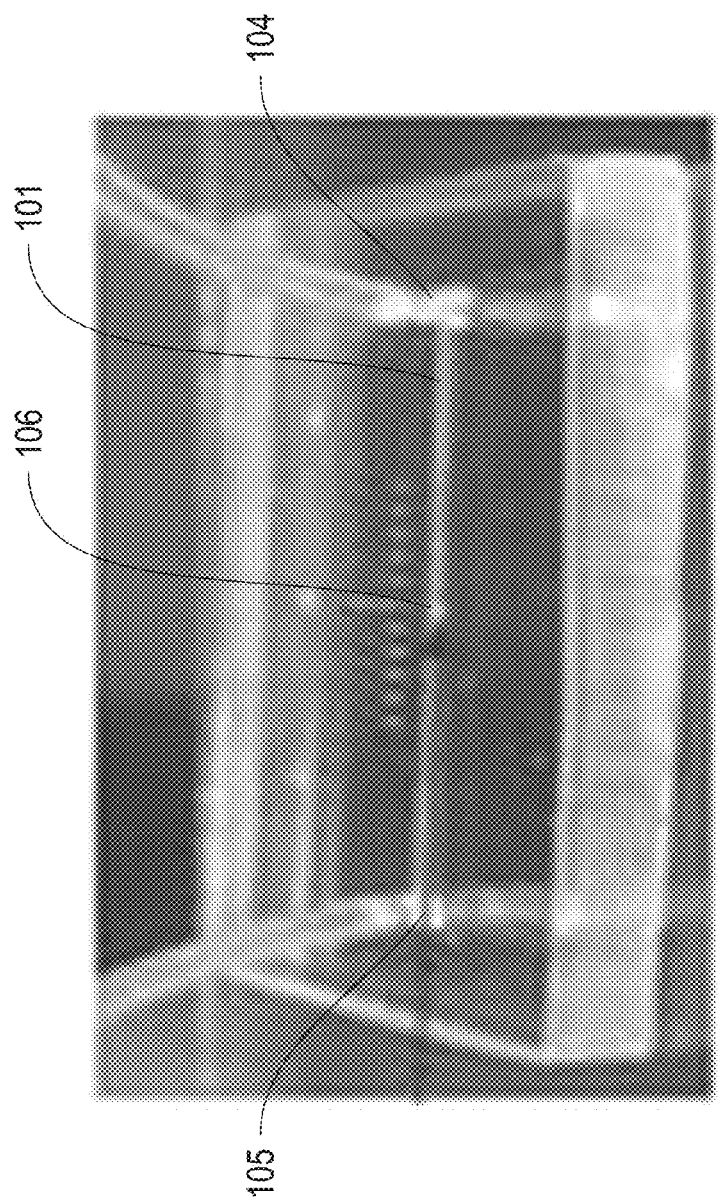
FIG. 2A is a perspective view of an example fluidic apparatus and biological sample.
Figure 2B:
FIG. 2B is a perspective view of an example microfluidic systems device.

FIGS. 2A and 2B show illustrative views of additional examples of a micro-scale fluidic apparatus for culturing and monitoring, ex vivo, pharmacologic and metabolic response in a biological sample. The apparatus may include a substrate, a channel located within the substrate for receiving the biological sample, a retaining element located within the channel for retaining the biological sample, a supply apparatus for supplying a fluid to the channel, a retrieval apparatus for retrieving fluid from the channel, and a visual field for providing visual observation of the channel. As illustrated in FIGS. 2A and 2B, the substrate may be fabricated from a polydimethylsiloxane (PDMS) with PDMS posts (or any of the other material identified above) on a glass substrate or other transparent cover slip for ease of microscopy. An example biological sample may be collected by FNAB using a 23-27 gauge needles, which typically provides a microscopic tumor fragments in the size of less than 500 micrometer (µm), and in some cases less than 300 µm, inner diameter in a 3-D structure. An example biological sample of a tumor cell may include tumor cells that intimately interact with the stromal components such as fibroblasts, endothelial cells, and immune cells. Fragments in that size (i.e., at or below 500 µm and in some cases at or below about 300 µm) allow substantially full exposure of tumor cells to a drug flowed through the channel through diffusion or interstitial flow through the tumor cells in the microfluidic conditions while preserving the histologic and cytologic architecture of the tumor. Thus, a biological sample can include one or more cell that is metabolically active or expected to be metabolically active. The one or more cell may also include a tumor cell. The one or more cell may also include a non-tumor cell. The one or more cell may also include a plurality of cells including at least one tumor cell and at least one non tumor cell.

The channel may be sized and configured to provide for the culture of a biological sample retrieved using fine-needle aspiration. The channels in the devices shown in FIGS. 2A and 2B are about 550 µm wide by about 120 µm in height and about 1 cm in length. The channels are sized and configured to provide for the growth of a three-dimensional cell culture of the biological sample. In a further example, the channels may be sized and configured to provide for growth of the biological sample on a multi-channel 3-D microfluidic cell culture chip.

The substrate shown in FIG. 2B includes a second channel for receiving a second biological sample. The second biological sample may be from the same, or different, tumor as included in the first channel. A second supply apparatus may supply a second fluid to the second channel. The second fluid may include the same, or different, fluid provided to the first sample in the first channel.

Figure 2C:
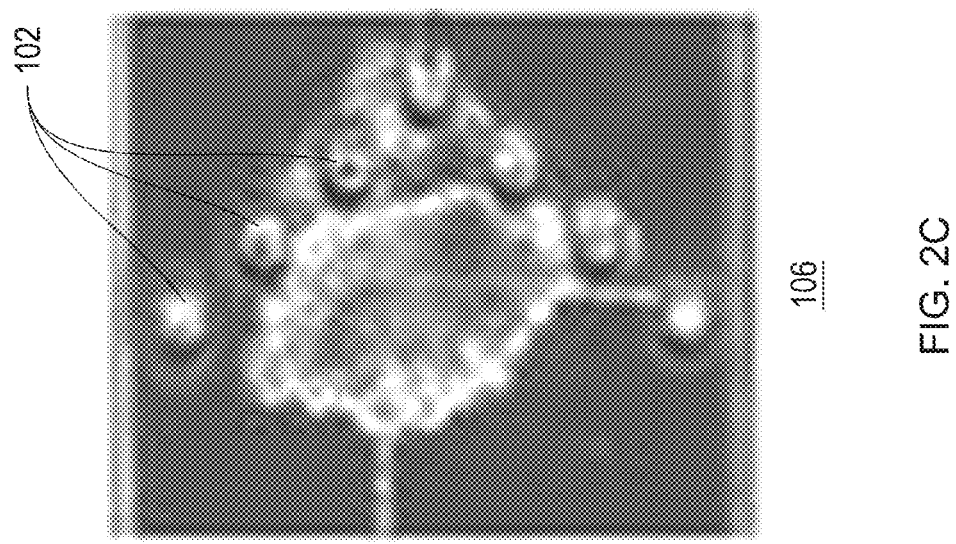
FIG. 2C is a view of a biological sample collected using fine needle aspirate biopsy retained within an example fluidic apparatus.

The channels include concave retaining barriers, similar to the concave retaining barriers shown in FIGS. 1B-1D, located within the channel for retaining the biological samples. For example, the retaining element may include a series of posts extending up from the floor of the channel. FIG. 2C is a micrograph of an example of a concave retaining barrier holding a tissue sample. The concave retaining barrier includes a series of posts in a V-shaped configuration pointed in the direction of the fluid flow. The posts, in the example, measure about 25 µm wide and about 100 µm in height, with about 25 µm lateral distance between posts.

Figure 3:
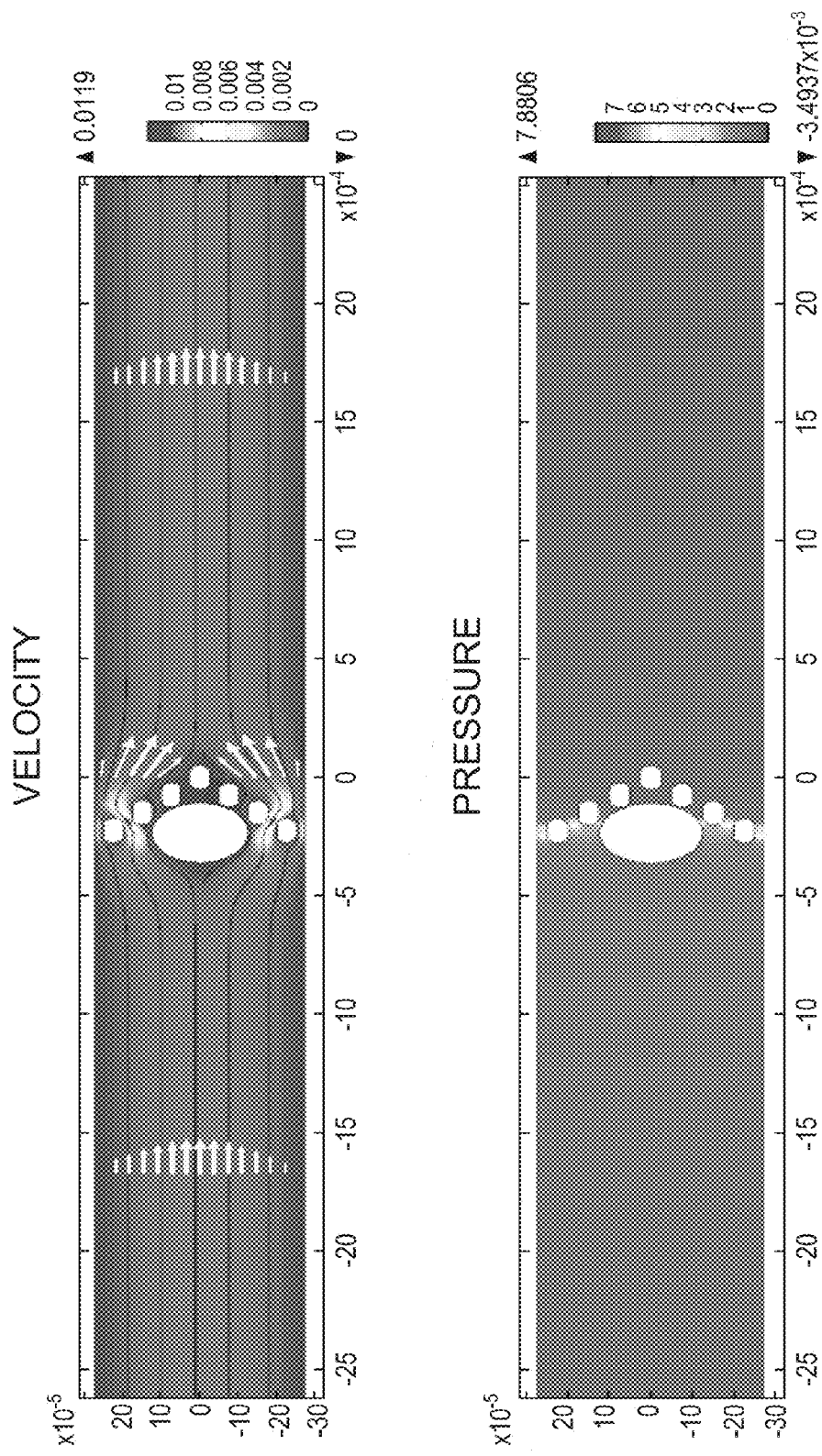
FIG. 3 is a model of the fluid dynamics of an example fluidics apparatus.

FIG. 3 shows a model of the fluid dynamics of the channel incorporated into the fluidic apparatus shown in FIG. 2A. The model depicts both the fluid velocity and pressure assuming a flow rate 100 µl/hour.

Using the micro-scale fluidic apparatus, culturing and monitoring, ex vivo, pharmacologic and metabolic response in a biological sample may be accomplished. First, a biological sample retrieved from the patient is provided to the fluidic apparatus. As outlined above, the biological sample may be retrieved using fine-needle aspiration and include a sample that is about or less than about 500 µm (or in some implementations 300 µm) in diameter. An example sample includes at least one of a tumor cell and a stroma cell.

The culture of the biological sample is provided in the channel of the fluidic apparatus. The culture may be a three-dimensional cell culture. The cells may be culture a multi-channel 3-D microfluidic cell culture chip.

A fluid is supplied to the biological sample inside the channel. The fluid may include, for example, a culture medium, a vehicle, and a drug. The fluid may be supplied by a continuous closed-loop system.

Figure 4:
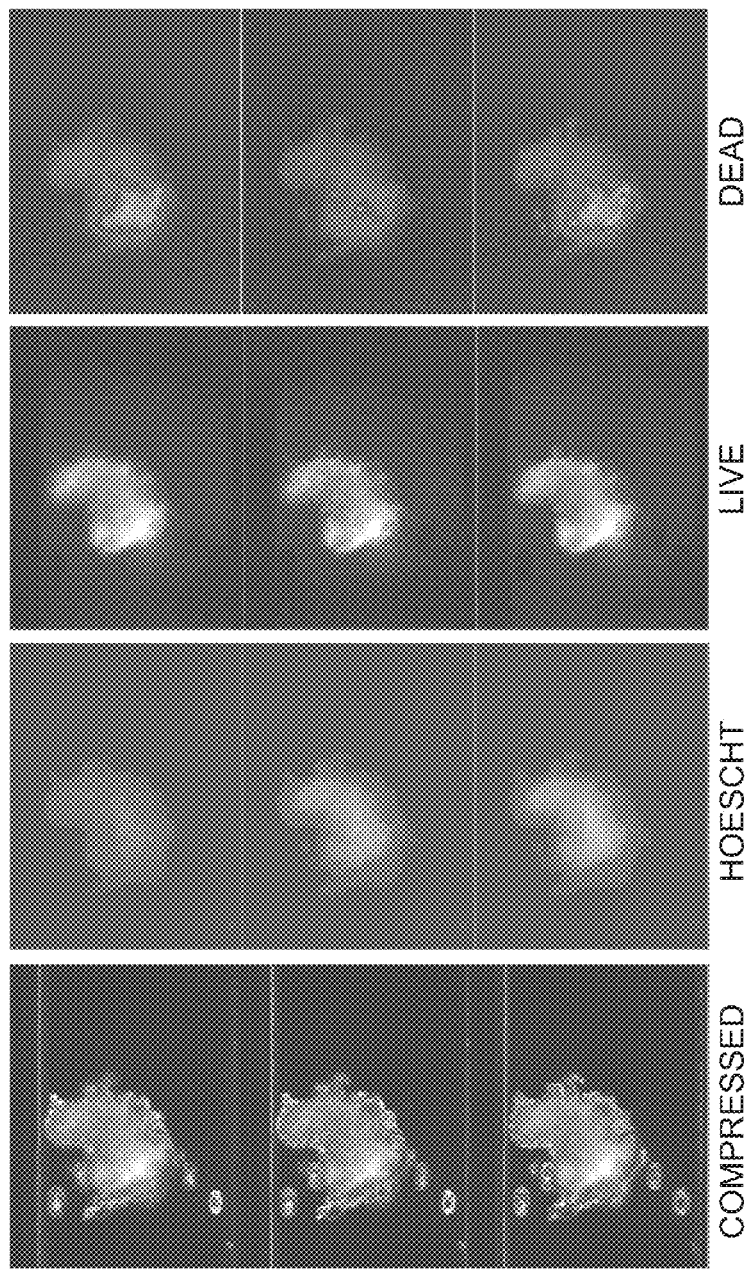
FIG. 4 is a table including example tumor samples subjected to a florescence stain.

The sample can be observed at a visual field provided on the fluidic apparatus. For example, the culture and the sample may be observed at the visual field using an inverted tissue culture microscope. A biomolecular sensor may be applied to the sample. For example, a florescence stain may be applied to the sample. In an example implementation illustrated in FIG. 4, fluorescence-based assays, such as LIVE/DEAD® assays (Invitrogen, Carlsbad, Calif.), may be used to evaluate cell death and viability. The Hoechst stain demonstrates nuclear structures and the compressed view shows the phase contrast views of the tumor FNAB samples in the microfluidic apparatus. Using this data, characteristic cell death metabolic profiles can be correlated along with microscopic analysis to indicate drug sensitivity by analyzing cultured media perfused through apparatus in contact with tumor. Metabolic analysis also includes methods for control versus drug response in the example microfluidic apparatus.

The methods, apparatuses, and systems described herein are may also be used to predict patient tumor response to chemotherapy and analyzes drug processing in tumor and other tissue ex vivo. The present system can be used for drug development, biomarker discovery and personalized therapy for individual patients to identify the most effective drug/drug combinations in a short period of time.

The methods, apparatuses, and systems may include flowing a fluid past the biological sample having at least one viable cell or cell that is expected to be viable, retrieving the fluid, and analyzing the fluid to determine at least one of a pharmacologic and a metabolic response of the sample. A pharmacologic response can be, for example, caused by flowing a fluid comprising a pharmacologic agent over the biologic sample. The response of the sample to the agent can be determined by analyzing the fluid for compounds, factors, or the like produced or elicited by a cell of the biologic sample by its interaction with the pharmacologic agent. The response can also be determined by visual analysis of the biologic sample, for example under the microscope, alone or in combination with detection of the fluid compounds, factors, or the like. An example pharmacologic agent is a chemotherapeutic agent. Similarly, a metabolic response can be, for example, caused by flowing a fluid comprising an agent that causes a metabolic response in the biologic sample over the biologic sample. The response of the sample to the agent can be determined by analyzing the fluid for compounds, factors, metabolic products, or the like produced or elicited by a cell of the biologic sample by its interaction with the agent. The response can also be determined by visual analysis of the biologic sample alone or in combination with detection of the fluid compounds, factors, or the like. An example, metabolic agent is glucose. Alternatively, or additionally, the analysis of the fluid indicates that the cell or cells of the sample are not viable.

Figure 5:
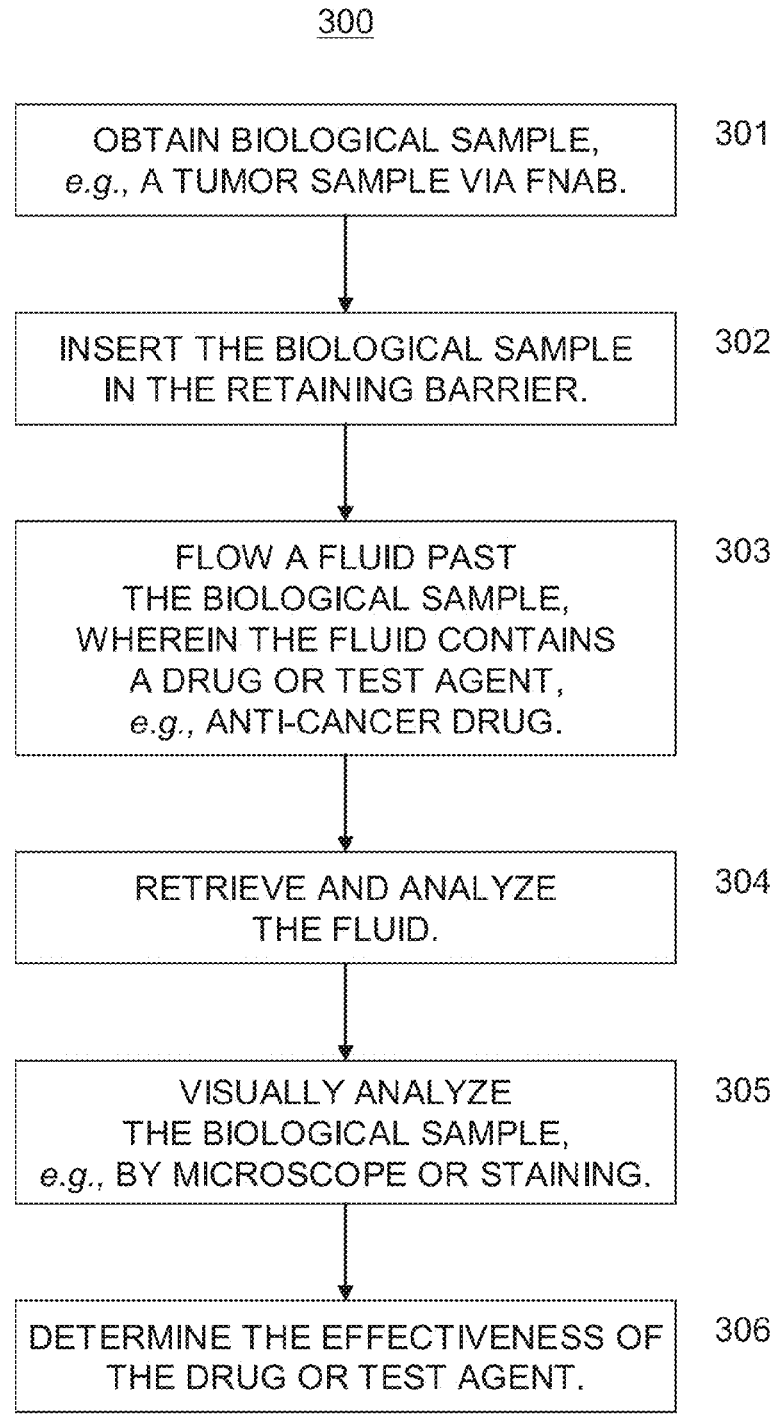
FIG. 5 is a flow chart showing an exemplary method for assaying a biological sample.

FIG. 5 is flowchart showing a non-limiting, exemplary method 300 for analyzing a biological sample using the disclosed microfluidic apparatus. First, a biological sample is obtained (step 301). For example, in some implementations, the biological sample is a tissue sample or tumor sample on the order of about 300 µm in diameter or smaller. In some implementations, the biological sample is obtained from FNAB or other extraction methods suitable for obtaining similarly sized tissue or tumor samples. The biological sample is inserted into the concave retaining barrier (step 302) located in a channel of a fluidic apparatus, such as the concave retaining barrier shown in FIG. 1C. Next, the biological sample is exposed to a flowing fluid (step 303). In some implementations, the fluid contains a drug or a compound. In some implementations, the biological sample is subject to continuous fluid flow in a closed loop for about 2-4 hours, about 4-8 hours, about 8-12 hours, about 12-24 hours, about 12-36 hour, or about 12-48 hours, or about 24-72 hours. In some implementations, the flow fluid is collected and analyzed (step 304). The flow fluid is analyzed for metabolites or other cellular byproducts related to drug or compound treatment. In some implementations, the flow fluid is collected about every 6 hours, 12 hours, 18 hours, 24 hours, 36 hours, or 48 hours. At the end of the assay, or periodically during the assay, the biological sample is subjected to visual analysis (step 305). Analysis of the flow fluid and visual analysis of the biological sample are used to determine the efficacy of the drug or compound (step 306).

An example system includes a three-dimensional (3-D) microfluidics platform for short-term culture of tumor and stroma cells obtained from FNAB, with the goal of using these for drug sensitivity testing by assessing full tumor response to chemotherapy by incorporating microscopic, pharmacodynamic, pharmacokinetic, proteomic, metabolomic and nucleic acid (including but not limited to DNA, mRNA and miRNA) analysis of tumor microenvironment and perfused media.

This FNAB microfluidics example system allows analysis of normal and disease-state tissue to drugs as a single tissue fragment or in a multi-tissue system on a chip format. This platform can be used for: drug development and drug testing for efficacy; biomarker discovery and validation in micofluidics; personalized therapy whereby tumor cells/tissue from individual patients can be tested for the most effective drug/drug combinations in a short period of time; personalized tumor microenvironment pharmacokinetic studies; and toxicology assays using liver and other non-tumoral tissue fragments.

Figure 6:
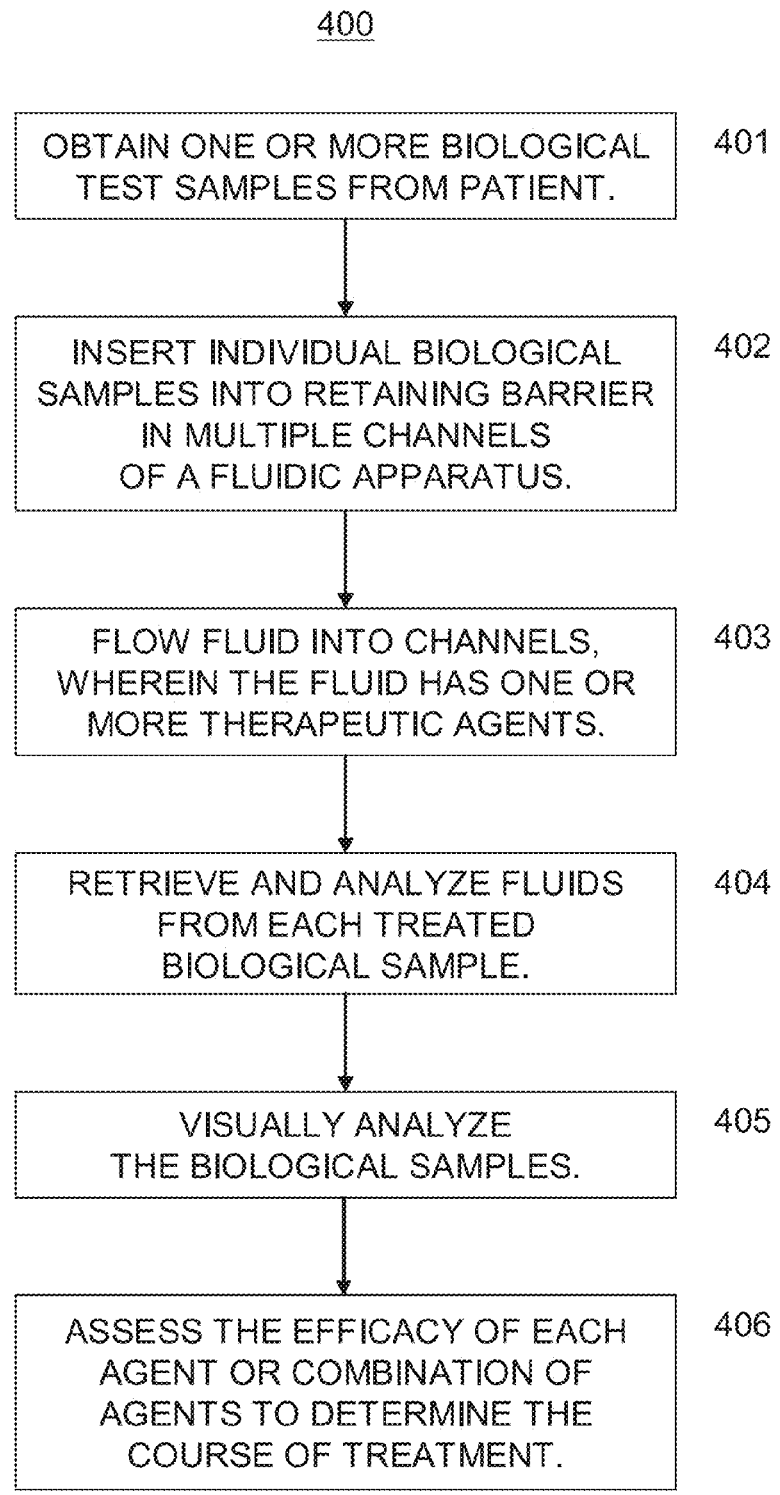
FIG. 6 is a flow chart showing an exemplary method for determining the personalized treatment for a patient.

FIG. 6 is a flow chart 400 showing how potential therapeutic agents are identified. First, one or more biological samples are obtained from a patient (step 401). The biological samples are then inserted into the retaining barriers of different channels in a fluidic apparatus (step 402). The channels are then subjected to fluid flow (step 403). In some implementations, the fluid in each channel contains a different therapeutic agent and/or different concentrations of the same therapeutic agent. Additionally, or alternatively, in some implementations, the a fluid can have one or more therapeutic agents. In some implementations, the biological sample is subject to continuous fluid flow in a closed loop for about 2-4 hours, about 4-8 hours, about 8-12 hours, about 12-24 hours, about 12-36 hour, or about 12-48 hours, or about 24-72 hours. In some implementations, the flow fluid is collected and analyzed (step 404). The flow fluid is analyzed for metabolites or other cellular byproducts related to the therapeutic agent or combination of agents. In some implementations, the flow fluid is collected about every 6 hours, 12 hours, 18 hours, 24 hours, 36 hours, or 48 hours. At the end of the assay, or periodically during the assay, the biological sample is subjected to visual analysis (step 405). In some implementations, a microscope or other optical sensor is used for visual and/or optical analysis. Analysis of the flow fluid and visual analysis of the biological sample are used to determine the efficacy of each therapeutic agent or combination of agents (step 406). Based on the results, a therapeutic course of treatment tailored specifically for the patient is determined (step 406).

EXAMPLES

The following examples are provided to more fully illustrate various implementations of the present technology. These examples should in no way be construed as limiting the scope of the invention.

Example 1—Use of Micro-Scale Fluidic Apparatus in Identifying Agents Useful in the Treatment of Osteosarcoma A micro-scale fluidic apparatus was used to investigate the response of fine needle biopsy samples (FNBA) of osteosarcoma to Gemcitabine and MK-1775, either alone or in combination for their effects in cell death and tumor shrinkage.

A. Micro-Scale Fluidic Apparatus

Eight micro-scale fluidic apparatuses of the present technology were fabricated from soft photolithography and bonded onto glass coverslip slides. The apparatuses were sterilized by ethylene oxide (EtO) gas. The structure of a fluidic apparatus is shown in FIGS. 2A and 2C. Each fluidic apparatus included a single channel, and the center of the channel contained a series of seven free standing post, collectively called the retaining element, which were used to retain the FNBA osteosarcoma sample (see FIG. 3A). Fluid flows into the channel by an inlet port and out of the channel by an outlet port.

B. Preparation of Osteosarcoma Sample

FNAB osteosarcoma samples were taken from xenograft mouse with patient-derived osteosarcoma using a 25-gauge needle. FNABs were processed and selected for viability by H&E staining procedures before use and individually loaded one into each retaining element and imaged by microscopy and measured for size (all FNABs assayed were ~300 µm in diameter).

C. Treatment of Osteosarcoma Sample Ex Vivo in Fluidic Apparatus

Eight FNAB samples were divided and treated as follows: two FNAB samples were treated with media only (control) (RPMI with 10% FBS, 300 mg/L L-glutamine, 2000 mg/L D-glucose, 2000 mg/L sodium bicarbonate); two FNAB samples were treated with 1 µM MK-1775 (SelleckChem, Houston, Tex.), a Wee 1 inhibitor, in cell culture media; two FNAB samples were treated with 3 µM gemcitabine (Eli Lilly, Indianapolis, Ind.), anti-cancer drug, in cell culture media; and two FNAB samples were treated with a combination of 1 µM MK-1775 and 3 µM gemcitabine in cell culture media.

The fluidic apparatuses were connected to their respective syringe pumps. The FNAB samples were first primed with several passes of culture media. After priming, each FNAB sample was subject to constant laminar flow at 100 µl/hr for 72 hours with their respective treatment. Media was collected every 24 hours and analyzed for caspase 3 and 7 and lactate dehydrogenase (LDH).

At the termination of each flow experiment each FNAB sample was microscopically visualized with Hoechst stain for nuclear counter stains by intercalating DNA and Sytox Green for cell death.

D. Treatment of Osteosarcoma Sample In Vivo

Xenograft mice bearing human osteosarcoma tumor were treated with vehicle, gemcitabine, MK-1775, or a combination of gemcitabine and MK-1775 for 15 days. Treatments were administered on day 1, 3, 8, and 10. FNAB samples were taken before (day 0) and at 6 and 24 hours after treatment. Cell extracts were prepared from the FNAB samples to assess expression levels of CDC2Y15, a target for MK-1775, by Western blot. After day 15, tumors were analyzed by $T_2$-weighted MRIs and paraffin sections of tumors were prepared to assess microscopic features of cell death by H&E-staining and to assess levels of cleaved-caspase 3.

E. Results

Figure 7A:
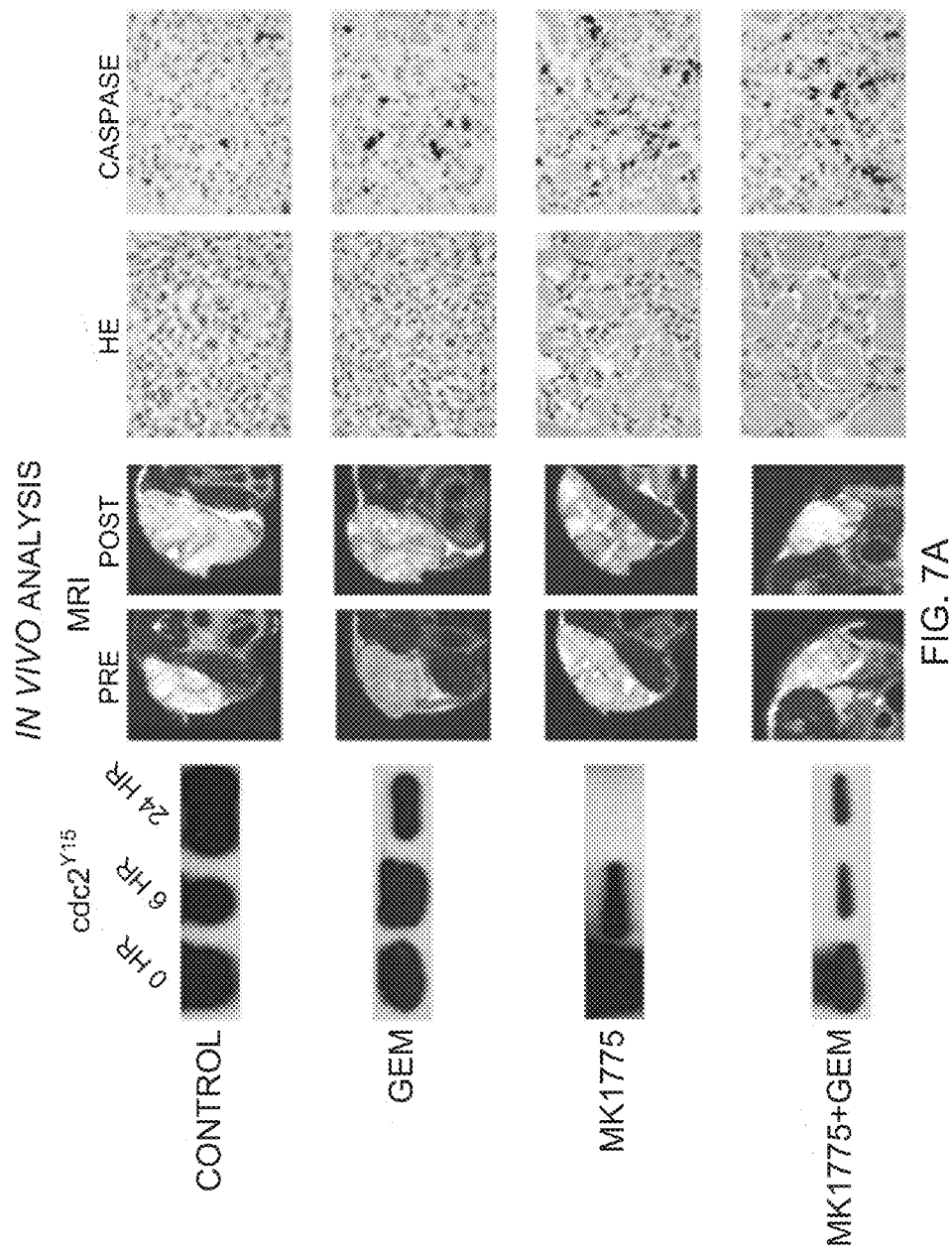
FIG. 7A is a table illustrating the effect of MK-1775 and gemcitabine in a xenograft mouse model in vivo.
Figure 7B:
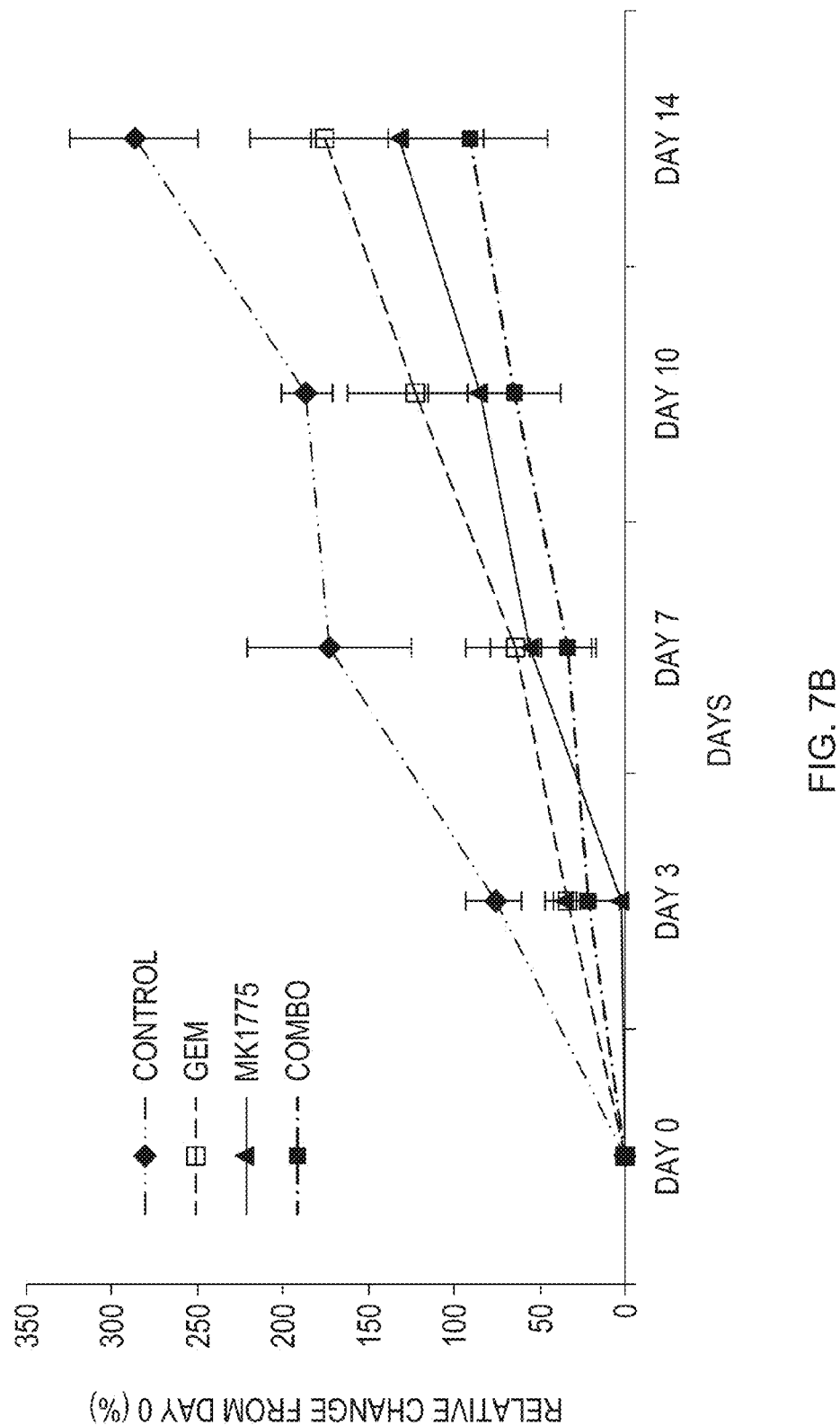
FIG. 7B is a table illustrating percent change of initial tumor volume as a function of time.

FIGS. 7A-B show the effect of MK-1775, gemcitabine, or combination of MK-1775 and gemcitabine in a xenograft mouse model in vivo. FIG. 7C shows the effect of MK-1775, gemcitabine, or combination of MK-1775 and gemcitabine using the fluidic apparatus model ex vivo.

FIG. 7A shows that MK-1775 and its combination with an anti-cancer drug gemcitabine lead to cell death in a patient-derived osteosarcoma xenograft mouse model in vivo. Column (a) shows that in vivo treatment of osteosarcoma xenograft mice with MK-1775 and combination treatment reduces expression levels of CDC2Y15 as compared to vehicle and gemcitabine treatments. Column (b) shows reduced tumor volume at day 15 in MK-1775-treated and combination-treated animals as compared to vehicle and gemcitabine treatments. Column (c) shows that MK-1775 and combination-treated animals have decreased DNA staining and high immunoreactivity to caspase 3 as compared to vehicle and gemcitabine treatments.

FIG. 7B shows that the percent change from the initial tumor volume (i.e., day 0) as a function of time, displaying the significant increase in tumor growth from day 0 to 15 in the control group versus the other treatment groups. The symbol (*) indicates statistical significance ($p<0.05$).

FIG. 7C shows the tumor response in microfluidic apparatus ex vivo. The results show that MK-1775 and its combination with gemcitabine lead to cell death in tumor fragments ex vivo. The FNAB samples were fully penetrated by drugs. Tumor cells were stained with HCS LIVE/DEAD® Green Kit (Life Technologies, Carlsband, Calif.) and images were obtained using inverted fluorescence microscope to assess dead (green) and alive (blue) cells.

The results show that the ex vivo treatment of osteosarcoma tumor samples with potential therapeutic agents using the fluidic apparatus produced similar results as in vivo treatment of osteosarcoma xenograph mice. Both models were able to identify that MK-1775 treatment or the combination of MK-1775 and gemcitabine treatment were able to induce apoptosis of the cancer cells. However, the ex vivo treatment was able to identify the efficacy of the agent or agents in a 72 hour period versus the 15 days of treatment the in vivo model require (the 15 days does not account for the time required for the nude mice to grow xenograft tumors).

Figure 8:
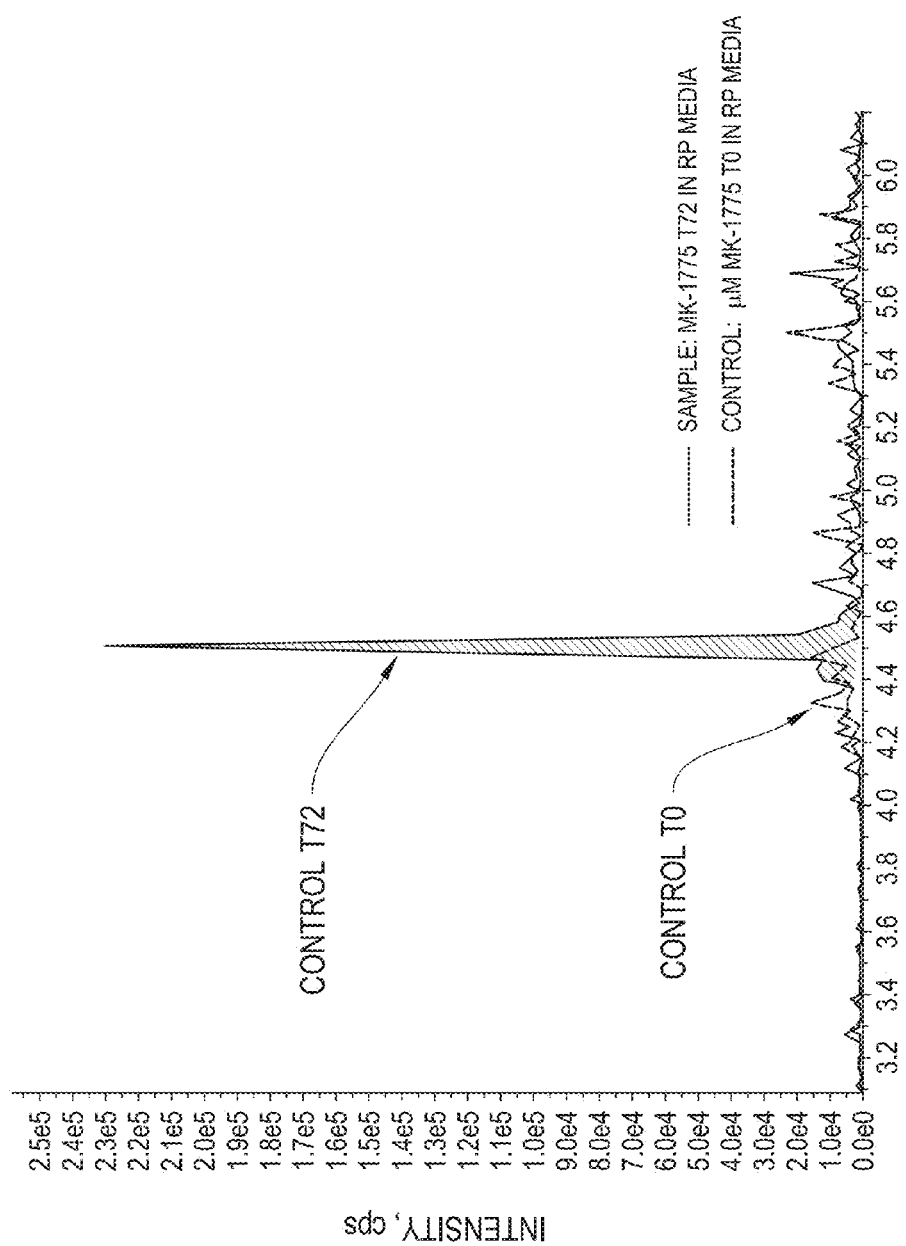
FIG. 8 provides an expanded view of an extracted ion chromatogram.

FIG. 8 provides an expanded view of an extracted ion chromatogram (XIC) from a potential metabolite highlighted against the background sample. Perfused fluid was collected from the fluidic apparatus as described in the above experiment performed with the FNAB samples (FIGS. 2A-C) to determine whether tumor-mediated drug processing and metabolism can be analyzed. Fluidic samples were prepared by filtration and analyzed by mass spectrometry. FIG. 8 demonstrates that tumor fragments obtained by FNAB from a patient-derived osteosarcoma xenograft model can incorporate drugs and convert the drugs into active and metabolized forms. Mass spectrometry data shows active metabolism of gemcitabine into its active form, triphosphate, and metabolism of MK-1775 into its metabolized forms. The same fluidic samples were analyzed for cell death utilizing active caspase ELISA kit, which revealed increased cell death upon MK-1775, but not gemcitabine treatment (data not shown). These results show that the fluidic apparatus is effective in perfusing a biological sample with drugs or therapeutic agents.

While the foregoing description and drawings represent the exemplary implementations of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed implementations are, therefore, to be considered in all respects as illustrative and not restrictive, the scope of the invention being indicated by the appended claims and not limited to the foregoing description.

It will be appreciated by those skilled in the art that changes could be made to the implementations described above without departing from the broad inventive concept thereof. It is understood, therefore, that this invention is not limited to the particular implementations disclosed, but it is intended to cover modifications within the spirit and scope of the present invention, as defined by the following claims.

What is claimed is:

1. A fluidic apparatus comprising:
   a substrate;
   a channel located within the substrate configured to receive a biological sample that is between 100 and 500 microns in diameter and to carry a fluid flow across the biological sample;
   a concave retaining barrier located within the channel to retain the biological sample, wherein the concave retaining barrier comprises a collection of posts arranged to form a barrier that is concave with respect to a direction of the fluid flow,
   wherein the geometry of the concave retaining barrier is configured to allow fluid flowing through the channel to induce interstitial flow of the fluid through the biological sample to perfuse the biological sample with the fluid while maintaining shear rates at the biological sample within a range of between about 0.375 and 0.500 dynes/cm$^2$.

2. The apparatus of claim 1, wherein the plurality of posts extend from the floor of the channel substantially to top of the channel.

3. The apparatus of claim 2, wherein the plurality of posts includes between three to ten free-standing posts extending substantially the full height of the channel and at least one embedded post extending out from a channel sidewall.

4. The apparatus of claim 3, wherein the concave retaining barrier comprises five free-standing posts and two embedded posts.

5. The apparatus of claim 2, wherein adjacent posts are spaced apart from one another to have a lateral separation across the width of the channel of the between about 20 μm about 40 μm.

6. The apparatus of claim 2, wherein the shortest distance between any two adjacent posts is between about 65 μm-85 μm.

7. The apparatus of claim 3, wherein an outer most free-standing post of the plurality of posts is spaced between about 65 μm-85 μm away from a nearest channel sidewall.

8. The apparatus of claim 2, comprising a fluid supply configured to flow a fluid through the channel.

9. The apparatus of claim 8, wherein the fluid supply comprises a closed loop fluid supply configured to reroute fluid already flowed through a distal end of the channel back through a proximal end of the channel.

10. The apparatus of claim 8, comprising a fluid extractor configured to extract a sample of the fluid after it has flowed through to channel.

11. The apparatus of claim 2, comprising an optical sensor for optically monitoring a state of a biological sample located within the retaining barrier.

* * * * *